(12) United States Patent
Kobayashi (10) Patent No.: US 10,073,061 B2
(45) Date of Patent: Sep. 11, 2018

(54) SENSOR APPARATUS (71) Applicant: KYOCERA CORPORATION, Kyoto (JP)

(72) Inventor: Kyohei Kobayashi, Kyoto (JP)

(73) Assignee: KYOCERA CORPORATION, Kyoto (JP)

( * ) Notice: Subject to any disclaimer, the term of this patent is extended or adjusted under 35 U.S.C. 154(b) by 0 days.

(21) Appl. No.: 15/305,788

(22) PCT Filed: Oct. 30, 2015

(86) PCT No.: PCT/JP2015/080862
§ 371 (c)(1),
(2) Date: Oct. 21, 2016

(87) PCT Pub. No.: WO2016/084554
PCT Pub. Date: Jun. 2, 2016

(65) Prior Publication Data
US 2017/0261470 A1 Sep. 14, 2017

(30) Foreign Application Priority Data

Nov. 29, 2014 (JP) .................................. 2014-242637

(51) Int. Cl.
*G01N 27/00* (2006.01)
*G01N 29/02* (2006.01)
*G01N 29/24* (2006.01)

(52) U.S. Cl.
CPC ............. *G01N 29/02* (2013.01); *G01N 29/24* (2013.01)

(58) Field of Classification Search
None
See application file for complete search history.

(56) References Cited

U.S. PATENT DOCUMENTS 5,130,257 A 7/1992 Baer et al.
5,283,037 A 2/1994 Baer et al.
(Continued)

FOREIGN PATENT DOCUMENTS

JP A 5-240762 9/1993
JP A 2006-184011 7/2006
(Continued)

OTHER PUBLICATIONS

International Search Report in International Application No. PCT/JP2015/080862, dated Jan. 26, 2016, in 2 pages.

*Primary Examiner* — Dennis Michael White
(74) *Attorney, Agent, or Firm* — Duane Morris LLP (57) ABSTRACT

A sensor apparatus includes an element substrate; a detecting section disposed on an upper surface of the element substrate, the detecting section including a reaction section having an immobilization film to detect an analyte, a first IDT electrode configured to generate an acoustic wave which propagates toward the reaction section, and a second IDT electrode configured to receive the acoustic wave which has passed through the reaction section; and a protective film which covers the first IDT electrode and the second IDT electrode. The upper surface of the element substrate includes a third region which is located between a first region where the first IDT electrode and the second IDT electrode are located and a second region where the reaction section is located. At least part of the third region is lower in level than the first region and the second region.

15 Claims, 7 Drawing Sheets

(56) References Cited

U.S. PATENT DOCUMENTS

| | | | |
|---|---|---|---|
| 5,306,644 | A | 4/1994 | Myerholtz et al. |
| 6,235,488 | B1 | 5/2001 | Tom-moy et al. |
| 2002/0192718 | A1 | 12/2002 | Tom-moy et al. |
| 2010/0109475 | A1* | 5/2010 | Lee ..................... G01N 29/022 310/313 C |
| 2010/0223999 | A1 | 9/2010 | Onoe |
| 2012/0146457 | A1 | 6/2012 | Goto et al. |

FOREIGN PATENT DOCUMENTS

| | | |
|---|---|---|
| JP | 2007-010378 A | 1/2007 |
| JP | 2010-233210 | 10/2010 |
| JP | A 2010-239477 | 10/2010 |
| JP | 2013-148572 | 8/2013 |
| WO | WO 2013/108608 | 7/2013 |

\* cited by examiner

SENSOR APPARATUS

TECHNICAL FIELD

The present invention relates to a sensor apparatus which is capable of measurement on the properties or constituents of an analyte liquid.

BACKGROUND ART

There is known a sensor apparatus which measures the properties or constituents of an analyte liquid by detecting a object to be detected object to be detected contained in the analyte liquid with use of a detecting element such as a surface acoustic wave device (refer to Patent Literatures 1 to 3, for example).

For example, in a sensor apparatus employing a surface acoustic wave device, a reaction section which undergoes reaction with a component contained in a sample of an analyte liquid, is disposed on a piezoelectric substrate, and the properties or constituents of the analyte liquid are detected by measuring variation in a surface acoustic wave propagating through the reaction section. Such a measurement method using the surface acoustic wave device or the like has the advantage over other measurement methods (for example, enzymatic method) in that it lends itself to simultaneous detection of a plurality of characteristics to be measured.

However, in such a conventional sensor apparatus, on the upper surface of the piezoelectric substrate, a pair of IDT electrodes and a region of the reaction section located between the paired IDT electrodes are equal in level, wherefore sufficient concentration of surface-acoustic-wave energy on the reaction section cannot be achieved with ease, which results in difficulties in detecting an object to be detected contained in an analyte with high sensitivity.

CITATION LIST

Patent Literature

Patent Literature 1: Japanese Unexamined Patent Publication JP-A 5-240762 (1993)
Patent Literature 2: Japanese Unexamined Patent Publication JP-A 2006-184011
Patent Literature 3: Japanese Unexamined Patent Publication JP-A 2010-239477

SUMMARY OF INVENTION

Technical Problem

Thus, there is a demand for a sensor apparatus which is capable of detecting an object to be detected contained in an analyte with excellent sensitivity.

Solution to Problem

A sensor apparatus according to an embodiment of the invention includes: an element substrate; a detecting section disposed on an upper surface of the element substrate, the detecting section including a reaction section having an immobilization film to detect an analyte, a first IDT electrode configured to generate an acoustic wave which propagates toward the reaction section, and a second IDT electrode configured to receive the acoustic wave which has passed through the reaction section; and a protective film which covers the first IDT electrode and the second IDT electrode, wherein the element substrate includes a third region which is located between a first region where the first IDT electrode and the second IDT electrode are located and a second region where the reaction section is located, at least part of the third region being lower in level than the first region and the second region.

Advantageous Effects of Invention

In accordance with the sensor apparatus according to the embodiment of the invention, the element substrate includes the third region which is located between the first region where the first IDT electrode and the second IDT electrode are located and the second region where the reaction section is located, and, at least part of the third region is lower in level than the first region and the second region. In this construction, a surface acoustic wave propagating between the first IDT electrode and the second IDT electrode is, during its passage through the relatively low third region and the relatively high second region (reaction section), increased in amplitude in the relatively high second region (reaction section). This makes it possible to detect an object to be detected contained in an analyte with high sensitivity.

DESCRIPTION OF EMBODIMENTS

Hereinafter, embodiments of a sensor apparatus according to the invention will be described with reference to drawings. In each drawing to be referred to in the following description, like constituent members are identified with the same reference symbols. Moreover, for example, the size of each member and the distance between the individual members are schematically shown in each drawing and may therefore differ from the actual measurements.

<Structure of Sensor Apparatus>

A sensor apparatus 100 according to an embodiment of the invention will be described with reference to FIGS. 1 to 6.

Figure 1:
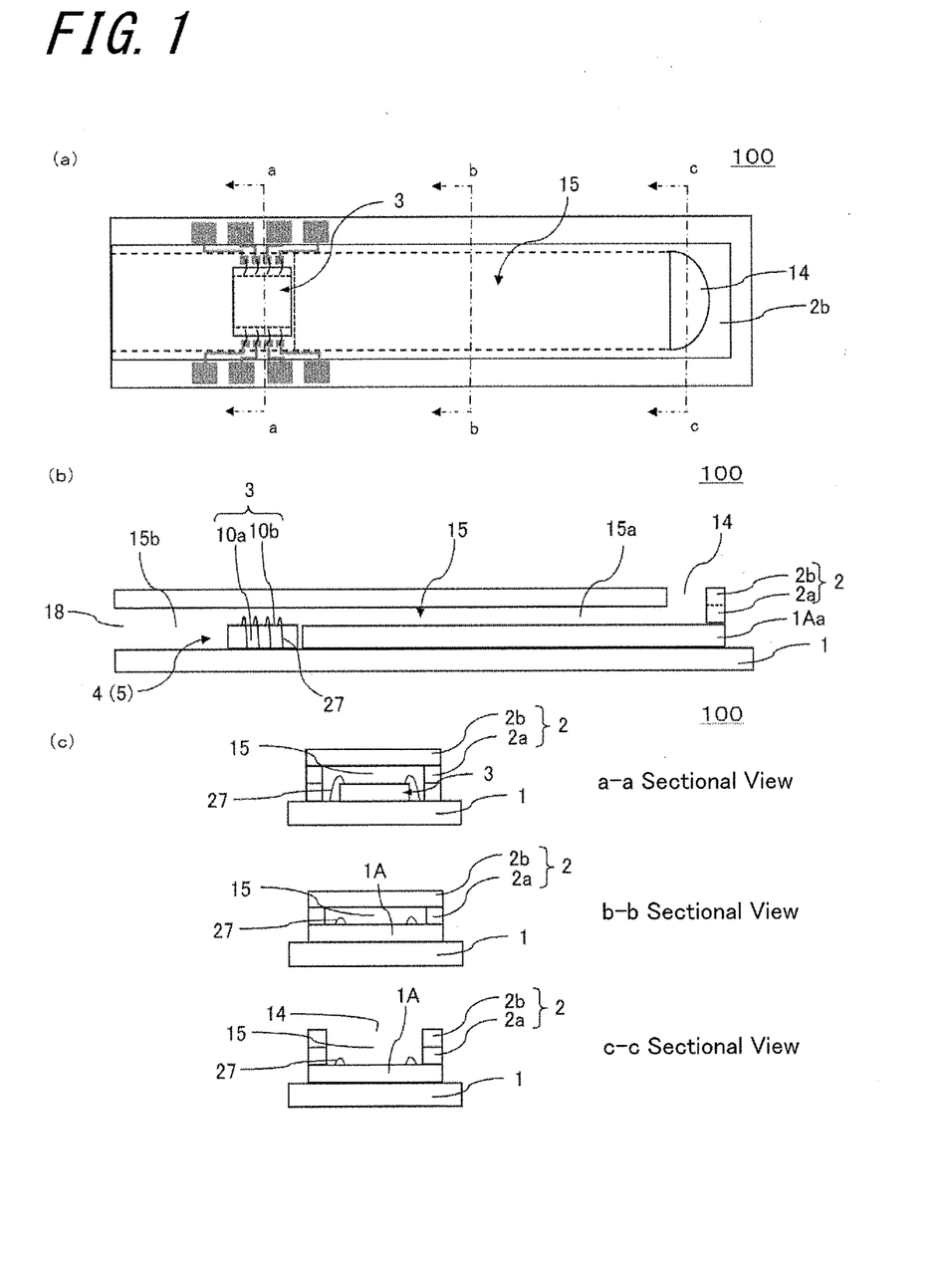
FIG. 1 is a view showing a sensor apparatus according to an embodiment of the invention, and FIG. 1(*a*) is a plan view, FIG. 1(*b*) is a lengthwise sectional view, and FIG. 1(*c*) is a widthwise sectional view.

As shown in FIG. 1, the sensor apparatus 100 according to the embodiment mainly comprises a first cover member 1, an intermediate cover member 1A, a second cover member 2, and a detecting element 3.

Specifically, as shown in FIG. 1(*b*), the sensor apparatus 100 has an inlet port 14 for admission of an analyte liquid, and a flow channel 15 which is in communication with the inlet port 14, is surrounded by the intermediate cover member 1A and the second cover member 2, and extends at least to a reaction section 13. In this embodiment, the intermediate cover member 1A and the second cover member 2 are greater in width than the detecting element 3. This allows an analyte liquid to flow so as to cover the entire surface of the detecting element 3 effectively.

FIG. 1(*c*) which shows sectional views of the construction shown in FIG. 1(*a*), wherein there are successively shown, in top-to-bottom order, a section taken along the line a-a, a section taken along the line b-b, and a section taken along the line c-c. The inlet port 14 is formed so as to pass through the second cover member 2 in a thickness direction thereof.

(First Cover Member 1)

Figure 2:
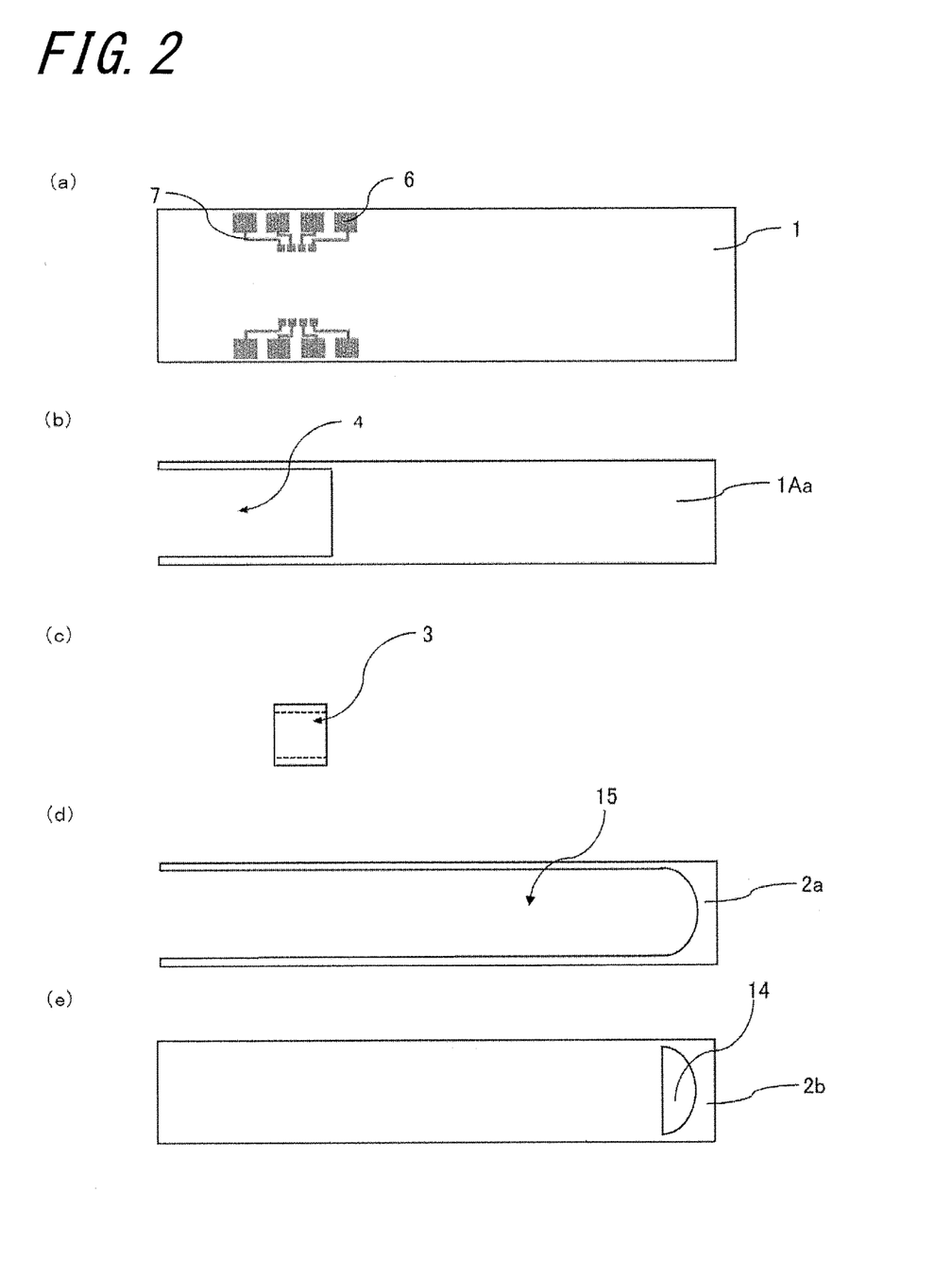
FIG. 2 is an exploded plan view of the sensor apparatus shown in FIG. 1.

As shown in FIGS. 1(*a*), 1(*b*) and FIG. 2(*a*), the first cover member 1 is shaped like a flat plate. The thickness of the first cover member 1 falls in the range of 0.1 mm to 1.5 mm, for example. The first cover member 1 has substantially a rectangular planar configuration. The longitudinal length of the first cover member 1 falls in the range of 1 cm to 8 cm, for example, and, the widthwise length of the first cover member 1 falls in the range of 1 cm to 3 cm, for example.

As the material for forming the first cover member 1, for example, a glass-epoxy material, paper, plastics, celluloid, ceramics, non-woven fabric, and glass can be used. The use of plastics is desirable from the standpoints of required strength and cost.

Moreover, as shown in FIGS. 1(*a*) and 2(*a*), on the upper surface of the first cover member 1 are formed a terminal 6 and a wiring line 7 routed from the terminal 6 to a position near the detecting element 3.

Figure 4:
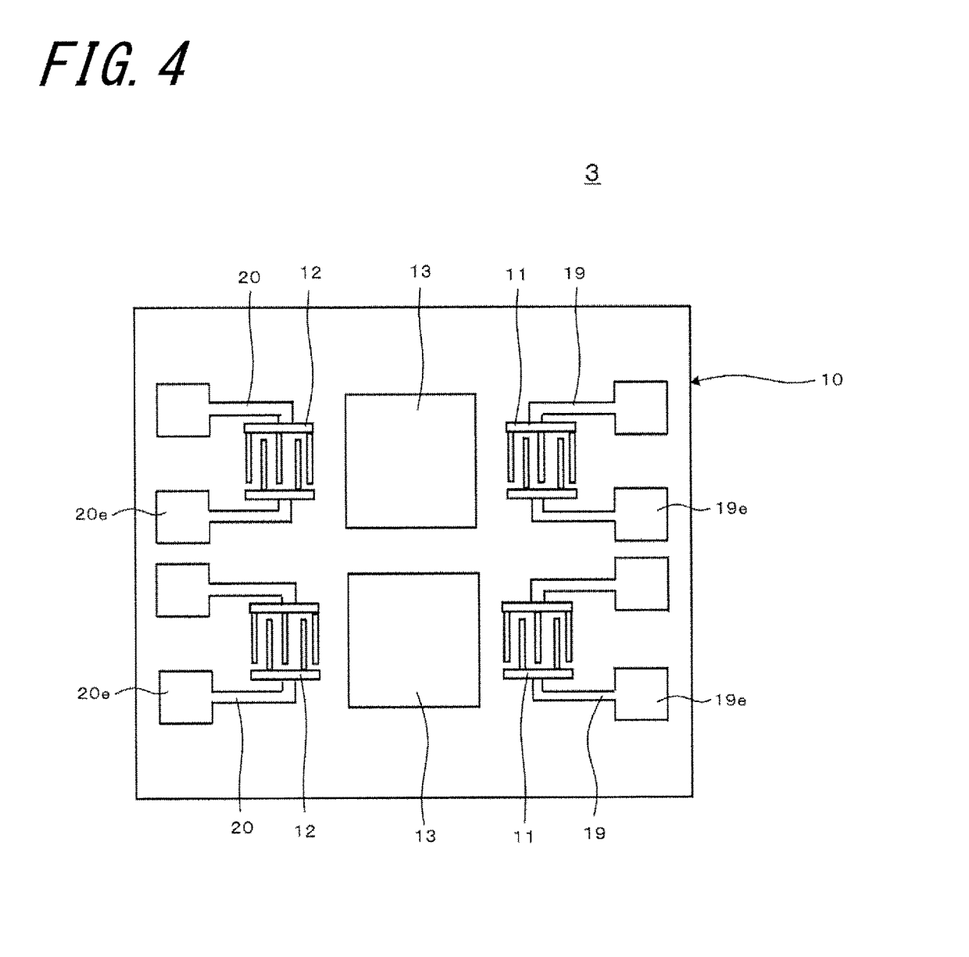
FIG. 4 is a plan view showing a detecting element of the sensor apparatus shown in FIG. 1.

The terminal 6 is formed on either side of the detecting element 3 in a width direction on the upper surface of the intermediate cover member 1A. Specifically, at least part of the terminals 6 arranged relative to the detecting element 3 located closer to the inlet port 14 than an inlet port 14-side end of the detecting element 3. Moreover, in the range of four terminals 6 placed in an array on one side of the detecting element 3 with respect to a direction longitudinally of the flow channel 15, the wiring lines 7 connected to two outer terminals 6, respectively, have substantially the same length, and, the wiring lines 7 connected to the other two inner terminals 6, respectively, have substantially the same length. This makes it possible to reduce variations in signals obtained by the detecting element 3 resulting from the difference in length between the wiring lines 7. In this case, with a construction in which the wiring lines 7 are connected so that a potential difference occurs between grounding (earthing) wiring, which is constituted by one pair of the wiring lines 7 having substantially the same length, and signal wiring, which is constituted by the other pair of the wiring lines 7 having substantially the same length, for example, upon application of a predetermined voltage from external measurement equipment to a first IDT electrode 11 as shown in FIG. 4 via the wiring line 7, a first extraction electrode 19, and so forth, it is possible to reduce the signal variations, and thereby achieve an improvement in detection reliability.

When measurement is made on the sensor apparatus 100 with external measuring equipment (not shown in the drawing), the terminal 6 and the external measuring equipment are electrically connected to each other. Moreover, the terminal 6 and the detecting element 3 are electrically connected to each other via the wiring line 7, for example.

A signal issued from the external measuring equipment is inputted to the sensor apparatus 100 via the terminal 6, and, a signal issued from the sensor apparatus 100 is outputted to the external measuring equipment via the terminal 6.

(Intermediate Cover Member 1A)

In this embodiment, as shown in FIG. 1(*b*), the intermediate cover member 1A is placed in juxtaposition to the detecting element 3 on the upper surface of the first cover member 1. Moreover, as shown in FIGS. 1(*a*) and 3(*c*), the intermediate cover member 1A and the detecting element 3 are arranged with a spacing. Note that the intermediate cover member 1A and the detecting element 3 may be arranged with their sides kept in contact with each other.

As shown in FIGS. 1(*b*) and 2(*b*), the intermediate cover member 1A has the form of a flat frame constructed of a flat plate having a recess-forming area 4, and, the thickness of the intermediate cover member 1A falls in the range of 0.1 mm to 0.5 mm, for example.

In this embodiment, as shown in FIG. 1(*b*), the recess-forming area 4 is an area located downstream of a first upstream portion 1Aa. The intermediate cover member 1A is joined to the flat plate-shaped first cover member 1, whereupon an element placement section 5 is defined by the first cover member 1 and the intermediate cover member 1A. That is, the upper surface of the first cover member 1 located inside the recess-forming area 4 becomes the bottom surface of the element placement section 5, and, the inner wall of the recess-forming area 4 becomes the inner wall of the element placement section 5.

Figure 3:
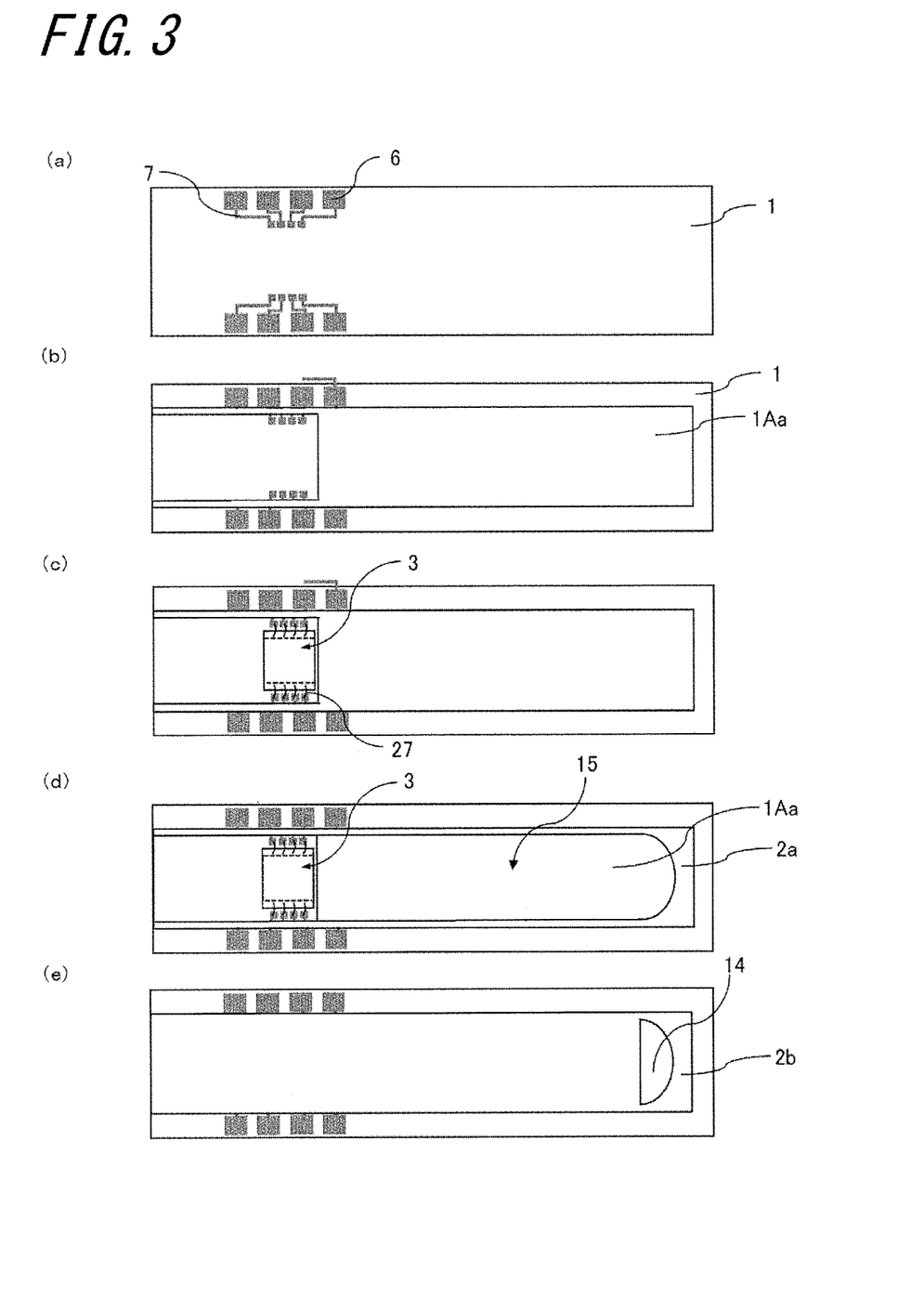
FIG. 3 is a plan view showing procedural steps to manufacture the sensor apparatus shown in FIG. 1.

As shown in FIGS. 1 and 3, in a region located downstream of the detecting element 3, the intermediate cover member 1A does not exist on the first cover member 1. This makes it possible to inhibit or reduce generation of bubbles in a part of the intermediate cover member 1A located downstream of the first upstream portion 1Aa. In consequence, an analyte liquid can be delivered in a bubble-free state onto the detecting element 3, thus achieving an improvement in sensitivity or accuracy in detection.

As the material for forming the intermediate cover member 1A, for example, resin (including plastics), paper, non-woven fabric, and glass can be used. More specifically, resin materials such as polyester resin, polyethylene resin, acrylic resin, and silicone resin are desirable for use. The first cover member 1 and the intermediate cover member 1A may be formed of either the same material or different materials.

Moreover, in this embodiment, the intermediate cover member 1A includes the first upstream portion 1Aa. As shown in FIGS. 1(*a*) and 1(*b*), when viewed from above, the detecting element 3 is located on the downstream side relative to the first upstream portion 1Aa. In this case, when an analyte liquid flows out over the detecting element 3 after passing through a part of the flow channel 15 which corresponds to the first upstream portion 1Aa, an excess of the analyte liquid over an amount of the analyte liquid required for measurement flows downstream, wherefore an adequate amount of the analyte liquid can be fed to the detecting element 3.

(Second Cover Member 2)

As shown in FIGS. 1(*b*) and 3(*e*), the second cover member 2 covers the detecting element 3, and is joined to the first cover member 1 and the intermediate cover member 1A. As shown in FIGS. 1(*b*) and 1(*c*), the second cover member 2 comprises a third substrate 2*a* and a fourth substrate 2*b*.

As the material for forming the second cover member 2, for example, resin (including plastics), paper, non-woven fabric, and glass can be used. More specifically, resin materials such as polyester resin, polyethylene resin, acrylic resin, and silicone resin are desirable for use. The first cover member 1 and the second cover member 2 may be formed of the same material. In this case, deformation resulting from the difference in thermal expansion coefficient between the first and second cover members can be minimized. The second cover member 2 may either be joined only to the intermediate cover member 1A or be joined to both of the first cover member 1 and the intermediate cover member 1A.

As shown in FIGS. 1(c), 3(c), and 3(d), the third substrate 2a is bonded to the upper surface of the intermediate cover member 1A. The third substrate 2a is shaped like a flat plate having a thickness of 0.1 mm to 0.5 mm, for example. The fourth substrate 2b is bonded to the upper surface of the third substrate 2a. The fourth substrate 2b is shaped like a flat plate having a thickness of 0.1 mm to 0.5 mm, for example. By joining the fourth substrate 2b to the third substrate 2a, as shown in FIG. 1(b), the flow channel 15 is formed on the lower surface of the second cover member 2. The flow channel 15 extends from the inlet port 14 to at least a region immediately above the reaction section 13, and has a rectangular sectional profile, for example. The third substrate 2a and the fourth substrate 2b may be formed of the same material, or, an unitary construction of the combined third and fourth substrates 2a and 2b may be used.

In this embodiment, as shown in FIG. 1(b), neither the intermediate cover member 1A nor the third substrate 2a exists at an end of the flow channel 15, and, a gap left between the fourth substrate 2b and the first cover member 1 serves as an air release hole 18. The air release hole 18 is provided to let air and so forth present in the flow channel 15 go out. The opening of the air release hole 18 may be given any shape which is capable of release of air present in the flow channel 15, and thus, for example, a circular shape or a rectangular shape may be adopted. For example, in the case of an air release hole 18 having a circular opening, the opening is designed to have a diameter of less than or equal to 2 mm, and, in the case of an air release hole 18 having a rectangular shape, the air release hole 18 is designed so that each side of the rectangle has a length of less than or equal to 2 mm.

The first cover member 1, the intermediate cover member 1A, and the second cover member 2 may be formed of the same material. In this case, since these members are substantially uniform in thermal expansion coefficient, it is possible to reduce deformation of the sensor apparatus 100 caused by the difference in thermal expansion coefficient among the members. Moreover, in the case of application of a biomaterial to the reaction section 13, some biomaterials are prone to quality degradation under external light such as ultraviolet rays. In this regard, it is advisable to use an opaque material having light-blocking capability as the material for forming the first cover member 1, the intermediate cover member 1A, and the second cover member 2. On the other hand, when the reaction section 13 is substantially free of external light-induced quality degradation, the second cover member 2 constituting the flow channel 15 may be formed of a nearly transparent material. In this case, the condition of an analyte liquid flowing through the interior of the flow channel 15 can be visually checked, thus permitting the combined use of an optical detection system.

(Detecting Element 3)

The detecting element 3 in the present embodiment will be described with reference to FIGS. 1 to 6, in particular, FIGS. 4 to 6.

Figure 5:
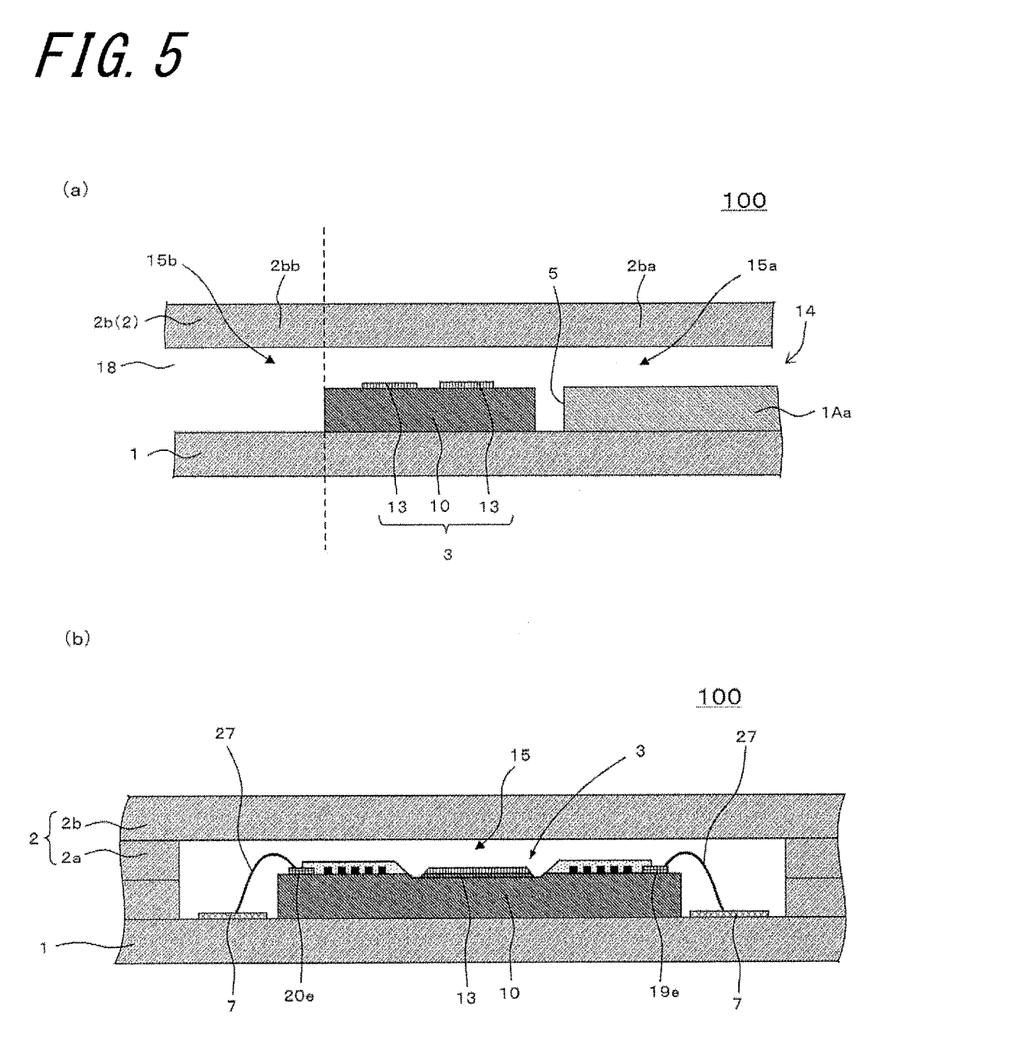
FIG. 5 is a sectional view showing the detecting element of the sensor apparatus shown in FIG. 1.
Figure 6:
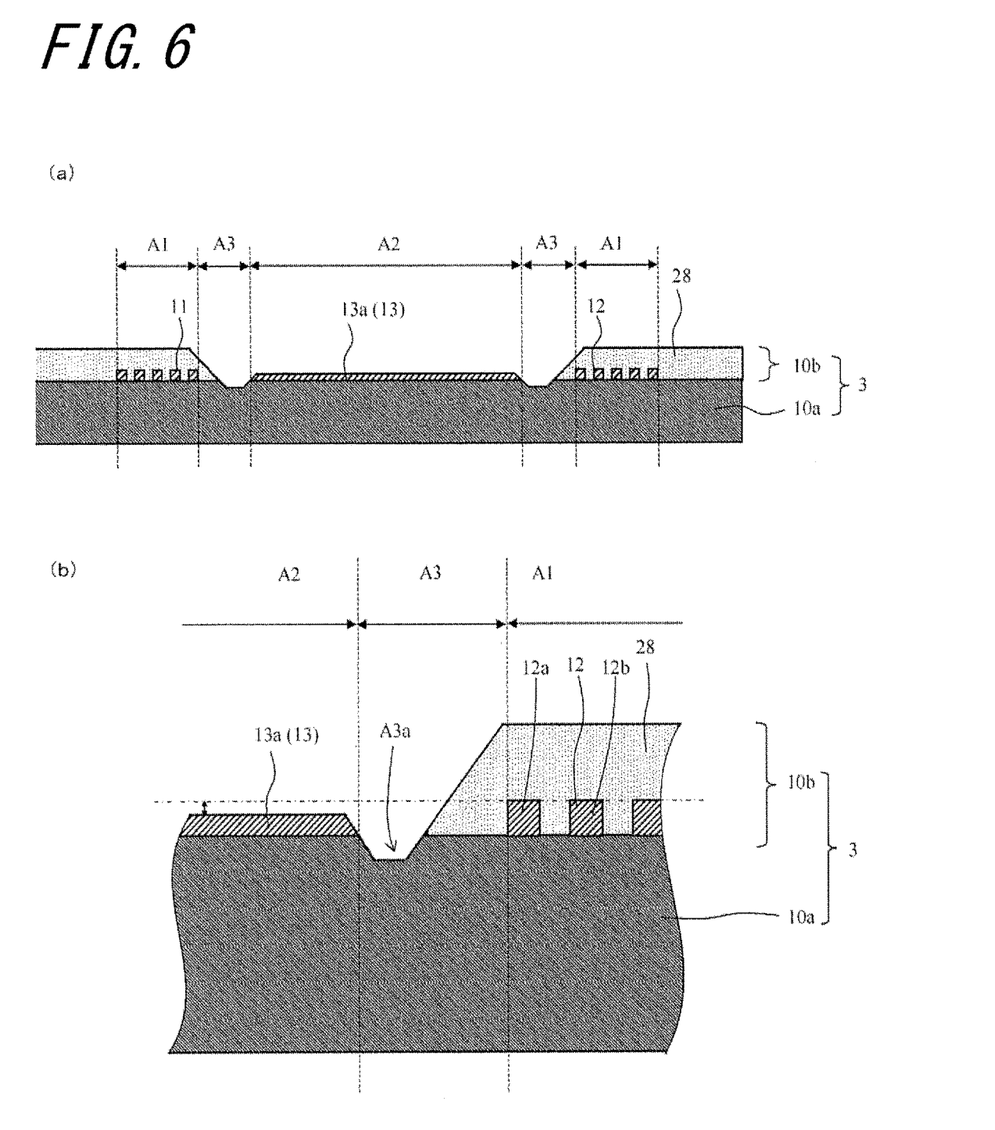
FIG. 6 is an enlarged sectional view showing part of the sensor apparatus shown in FIG. 5.

FIG. 6 is an enlarged sectional view showing part of the sensor apparatus shown in FIG. 5, and more specifically FIG. 6(a) is an enlarged view of the principal portion of the detecting element shown in FIG. 5(b), and FIG. 6(b) is an enlarged view of part of the principal portion of FIG. 6(a).

As shown in FIG. 6, the detecting element 3 generally comprises an element substrate 10a disposed on the upper surface of the first cover member 1, and at least one detecting section 10b, disposed on the upper surface of the element substrate 10a, for detecting an object to be detected (detection target) contained in an analyte liquid.

Specifically, as shown in FIG. 6, the detecting element 3 in this embodiment comprises: the element substrate 10a; the detecting section 10b disposed on the upper surface of the element substrate 10a, the detecting section 10b including the reaction section 13 having an immobilization film 13a to detect an object to be detected, a first IDT (Inter-Digital Transducer) electrode 11 configured to generate an acoustic wave which propagates toward the reaction section 13, and a second IDT electrode 12 configured to receive the acoustic wave which has passed through the reaction section 13; and a protective film 28 which covers the first IDT electrode 11 and the second IDT electrode 12. The element substrate 10a comprises a third region A3 which is located between a first region A1 where the first IDT electrode 11 and the second IDT electrode 12 are located, and a second region A2 where the reaction section 13 is located. At least part of the third region A3 is lower in level than the first region A1 and the second region A2. The detecting section 10b includes, in addition to the first IDT electrode 11, the reaction section 13, and the second IDT electrode 12, the protective film 28, a first extraction electrode 19, a second extraction electrode 20, and so forth.

(Element Substrate 10a)

The element substrate 10a is constructed of a substrate of single crystal having piezoelectric properties such for example as quartz, lithium tantalate ($LiTaO_3$) single crystal, or lithium niobate ($LiNbO_3$) single crystal. The planar configuration and dimensions of the element substrate 10a are suitably determined. The element substrate 10a has a thickness of 0.3 mm to 1 mm, for example.

In this embodiment, as shown in FIG. 6, the element substrate 10a has the first region A1 where the first IDT electrode 11 and the second IDT electrode 12 are located, the second region A2 where the reaction section 13 is located, and the third region A3 which is located between the first region A1 and the second region A2. At least part of the third region A3 is lower in level than the first region A1 and the second region A2. In this case, SAW (Surface Acoustic Wave) propagating between the first IDT electrode 11 and the second IDT electrode 12 is, during its passage through the relatively low third region A3 and the relatively high second region A2 (reaction section 13), increased in amplitude in the relatively high second region A2 (reaction section 13). This makes it possible to achieve detection of an object to be detected with high sensitivity.

As shown in FIG. 6(b), in the element substrate 10a, at least part of the third region A3 is defined by a recess A3a, and, the recess A3a is tapered so as to narrow gradually with approaching toward a bottom thereof as viewed in a lateral section thereof. In this case, in the vicinity of the upper surface of the element substrate 10a, there is a gentle profile change of the boundary with the immobilization film 13a in a SAW propagation direction. This makes it possible to reduce SAW reflection at the boundary, and thereby reduce losses of electric signals. In the recess A3a constituting at least part of the third region A3, given that the wavelength of SAW propagating between the first IDT electrode 11 and the second IDT electrode 12 is $\lambda$, then the bottom of the recess A3a may be positioned at a level which is $0.02\lambda$ or below lower than the upper surfaces of the first region A1 and the second region A2. Moreover, the bottom of the recess A3a may be designed to be greater in surface roughness than the upper surface of the immobilization film 13a.

The surface roughness of each constituent element is determined by measurement using arithmetic average roughness Ra. In cases where the protective film 28 or other film component is disposed on a measurement target, for surface roughness measurement, for example, graphic analyses of the sectional profile of the measurement target are performed on the basis of a photograph of the section obtained by means of SEM (Scanning Electron Microscopy), TEM (Transmission Electron Microscopy), or otherwise. Moreover, when direct measurement of the measurement target is possible, the measurement may be effected with use of a commonly-used surface-roughness meter of contact type or non-contact type. The conditions described hold in what follows unless otherwise specified.

In this embodiment, the surface roughness of the upper surface of the immobilization film 13a is greater than the surface roughness of a part of the element substrate 10a on which the immobilization film 13a is disposed. In this case, for example, in immobilizing aptamers and antibodies, which will hereafter be described, onto the surface of the element substrate 10a, the aptamers and antibodies can be bonded to the surface of the immobilization film 13a with higher bindability, thus enabling high-density immobilization. This makes it possible to improve detection sensitivity of the object to be detected.

(IDT Electrodes 11 and 12)

As shown in FIGS. 4 and 6, the first IDT electrode 11 comprises a pair of comb electrodes. Each comb electrode includes two bus bars opposed to each other and a plurality of electrode fingers each extending from corresponding one of the bus bars toward the other. A pair of the comb electrodes is disposed so that the plurality of electrode fingers are arranged in an interdigitated pattern. The second IDT electrode 12 is similar in configuration to the first IDT electrode 11. The first IDT electrode 11 and the second IDT electrode 12 constitute a transversal IDT electrode.

The first IDT electrode 11 is intended for generation of predetermined surface acoustic wave, and the second IDT electrode 12 is intended for reception of the SAW generated in the first IDT electrode 11. The first IDT electrode 11 and the second IDT electrode 12 are positioned on the same straight line so that the SAW generated in the first IDT electrode 11 can be received by the second IDT electrode 12. Frequency response characteristics can be designed on the basis of the number of the electrode fingers of the first IDT electrode 11 and the second IDT electrode 12, the distance between the adjacent electrode fingers, the crossing width of the electrode fingers, etc., used as parameters.

There are various modes of vibration for SAW to be excited by the IDT electrode. In the detecting element 3 according to the embodiment, for example, a vibration mode of transversal waves called SH waves is utilized. The frequency of SAW may be set within the range of several megahertz (MHz) to several gigahertz (GHz), for example. It is advisable to set the SAW frequency within the range of several hundred MHz to 2 GHz from the practicality standpoint, and also in the interest of miniaturization of the detecting element 3 that will eventually be conducive to miniaturization of the sensor apparatus 100. The thicknesses and lengths of predetermined constituent elements in the embodiment will be described with respect to the case where the center frequency of SAW falls in a several hundred MHz range.

The first IDT electrode 11 and the second IDT electrode 12 may be of a single-layer structure composed of, for example, a gold thin layer, or may be of a multilayer structure such as a three-layer structure composed of a titanium layer, a gold layer, and a titanium layer, or a three-layer structure composed of a chromium layer, a gold layer, and a chromium layer, in the order named, from the element-substrate 10a side.

A thickness of the first IDT electrode 11 and the second IDT electrode 12 may be set to fall within the range of $0.005\lambda$ to $0.015\lambda$, for example.

An elastic member may be disposed externally of the first IDT electrode 11 and the second IDT electrode 12 in a SAW propagation direction (width direction) to reduce SAW reflection.

(Reaction Section 13)

As shown in FIGS. 4 and 6, the reaction section 13 is disposed between the first IDT electrode 11 and the second IDT electrode 12.

In this embodiment, the reaction section 13 comprises the immobilization film 13a (for example, a metallic film) formed on the upper surface of the element substrate 10a, and a reactant immobilized on the upper surface of the immobilization film 13a for reaction with an object to be detected. The reactant is suitably selected depending on an object to be detected which is a detection target. For example, when the object to be detected is a specific cell or living tissue present in an analyte liquid, an aptamer composed of a nucleic acid or a peptide can be used as the reactant. For example, in this embodiment, while a reaction between the reactant and the object to be detected may be a binding reaction of the object to be detected and the reactant such as a chemical reaction or an antigen-antibody reaction, the reaction is not so limited, but may be a binding reaction of the object to be detected and the reactant under the interaction of the object to be detected with the reactant, or an adsorption reaction of the object to be detected to the reactant. Exemplary of a reactant which can be used for the reaction section 13 in the embodiment is one which causes, by its presence, variation in surface-acoustic-wave characteristics according to the type or content of the object to be detected when an analyte is brought into contact with the reaction section 13. The reaction section 13 is intended for causing reaction with an object to be detected contained in an analyte liquid, and, more specifically, upon contact of an analyte liquid with the reaction section 13, a specific object to be detected contained in the analyte liquid is bound to an aptamer adapted to the object to be detected.

The immobilization film 13a (metallic film) may be of a single-layer structure composed of, for example, a gold layer, or may be of a multilayer structure such as a two-layer structure composed of a titanium layer and a gold layer situated on the titanium layer or a two-layer structure composed of a chromium layer and a gold layer situated on the chromium layer. Moreover, the immobilization film 13a may be formed of the same material as a material used for the first IDT electrode 11 and the second IDT electrode 12. In this case, the immobilization film 13a and the first and second IDT electrodes 11 and 12 can be formed in the same process step. Instead of the above-mentioned metallic film, for example, an oxide film such as a $SiO_2$ film or $TiO_2$ film may be used as the material of construction of the immobilization film 13a.

Given that the first IDT electrode 11, the second IDT electrode 12, and the reaction section 13 arranged in the width direction of the flow channel are grouped into a set, then, as shown in FIG. 4, two sets are provided in the sensor apparatus 100 according to the embodiment. In this case, by designing the reaction section 13 of one of the sets and the reaction section 13 of the other to undergo reaction with different objects to be detected, it is possible to detect two different objects to be detected by a single sensor apparatus.

In this embodiment, as shown in FIG. 6(b), the upper surface of the immobilization film 13a is at a higher level than the upper surface of the first region A1 of the element substrate 10a where the first IDT electrode 11 and the second IDT electrode 12 are located. In this case, in the reaction section 13, energy of SAW propagating between the first IDT electrode 11 and the second IDT electrode 12 tends to be concentrated on the immobilization film 13a, wherefore an object to be detected can be detected with high sensitivity.

Moreover, as shown in FIG. 6(b), the upper surface of the immobilization film 13a is positioned at a lower level than at least one of the upper surface of the first IDT electrode 11 and the upper surface of the second IDT electrode 12. In this case, in the reaction section 13, energy of SAW propagating between the first IDT electrode 11 and the second IDT electrode 12 is readily concentrated on the immobilization film 13a, wherefore an object to be detected can be detected with higher sensitivity.

As shown in FIG. 6(b), the upper surface of the immobilization film 13a may be at a level which is 0.01λ or below lower than the upper surface of the first IDT electrode 11 and the upper surface of the second IDT electrode 12. In this case, in the reaction section 13, energy of SAW propagating between the first IDT electrode 11 and the second IDT electrode 12 tends to be concentrated on the upper surface of the immobilization film 13a, wherefore an object to be detected can be detected with high sensitivity.

Moreover, an end of the immobilization film 13a located on at least one of a side of the first IDT electrode 11 and a side of the second IDT electrode 12 comprises a lower end part and an upper end part, the lower end part being closer to the at least one than the upper end part when viewed in a lateral section. Moreover, an end of the immobilization film 13a located on at least one of a side of the first IDT electrode 11 and a side of the second IDT electrode 12 comprises a lower end part and an upper end part, the end being inclined so as to approach the corresponding one of the first IDT electrode 11 and the at least one as the end going from the upper end part to the lower end part when viewed in a lateral section. In this case, in the vicinity of the upper surface of the element substrate 10a, since there is a gentle profile change of the boundary with the immobilization film 13a in the SAW propagation direction, it is possible to reduce surface-acoustic-wave reflection at the boundary, and thereby reduce losses of electric signals. Note that the end of the immobilization film 13a may be inclined at an inclination angle which is smaller than the angle of inclination of the protective film 28 as will hereafter be described.

A thickness of the immobilization film 13a may be set to fall within the range of 0.005λ to 0.015λ, for example. In this embodiment, as shown in FIG. 6(b), the thickness of the immobilization film 13a is smaller than at least one of the thickness of the first IDT electrode 11 and the thickness of the second IDT electrode 12. In this case, even if the immobilization film 13a has a relatively small thickness, in the reaction section 13, losses of energy of SAW propagating between the first IDT electrode 11 and the second IDT electrode 12 can be reduced. In addition to that, since the SAW energy tends to be concentrated on the immobilization film 13a, it is possible to detect an object to be detected with high sensitivity.

The surface roughness of the upper surface of the immobilization film 13a is greater than at least one of the surface roughness of the upper surface of the first IDT electrode 11 and the surface roughness of the upper surface of the second IDT electrode 12. In this case, in the reaction section 13, it is possible to immobilize aptamers, antibodies, etc. at high densities, and thereby improve the detection sensitivity even further. The surface roughness of the upper surface of the immobilization film 13a, which falls in the range of, for example, 2.0 to 5.0 nm in terms of arithmetic average roughness Ra, may be obtained by measuring the upper surface, as a measurement target, using a commonly-used surface-roughness meter of contact type or non-contact type. Moreover, the surface roughness of the upper surface of each of the first IDT electrode 11 and the second IDT electrode 12 may be obtained by measuring the upper surface, as a measurement target, of either any of comb electrode portions or a portion connecting these electrode portions using a commonly-used surface-roughness meter of contact type or non-contact type.

(Protective Film 28)

As shown in FIG. 6, the protective film 28 is located on the upper surface of the element substrate 10a so as to cover the first IDT electrode 11 and the second IDT electrode 12. This makes it possible to inhibit an analyte liquid from contact with the first IDT electrode 11 and the second IDT electrode 12, and thereby retard corrosion of the IDT electrodes caused by oxidation, for example. Examples of materials used for the protective film 28 include silicon oxide, aluminum oxide, zinc oxide, titanium oxide, silicon nitride, and silicon. Such a material is properly used as a major constituent, namely a component constituting the greatest proportion in mass, of the protective film 28-forming material, and is therefore not defined as the constituent material when mixed merely, for example, as impurities in very small amounts in the protective film 28-forming material.

In this embodiment, as shown in FIG. 6(b), the protective film 28 is also located in a region between the reaction section 13 (the immobilization film 13a) and at least one of the first IDT electrode 11 and the second IDT electrode 12, that is; the third region A3. This makes it possible to inhibit the side portion of the IDT electrode located on the immobilization film 13a side from contact with an analyte liquid. In this construction, as shown in FIG. 6(b), the protective film 28 is located without contact with and apart from the reaction section 13 (the immobilization film 13a). This helps reduce the influence of the protective film 28 upon the sensitivity of the reaction section 13 (the immobilization film 13a) to SAW.

Moreover, part of the protective film 28 is located in a part of the third region A3, the part of the third region being located between the recess A3a and at least one of the first IDT electrode 11 and the second IDT electrode 12. In this case, the presence of the protective film 28 makes it possible to suppress generation of electric direct waves in the region between the first IDT electrode 11 and the second IDT electrode 12, and thereby reduce signal noise.

Moreover, as shown in FIG. 6(b), an end of the protective film 28 located on a side of the reaction section 13 (the immobilization film 13a) comprises a lower end part and an upper end part, the lower end part being closer to the reaction section 13 (the immobilization film 13a) than the upper end part when viewed in a lateral section. As used herein, the language "lateral section" means, as will be seen from FIG. 1(b) for example, a section taken along the line a-a of FIG. 1(a) or a line perpendicular to the line a-a, looking from the side of the sensor apparatus. Moreover, the language "an end of the protective film 28 located on a side of the reaction section 13" means an end of the protective film 28 opposite the end located on at least one of the first IDT electrode 11 side and the second IDT electrode 12 side under the condition where, for example, as described above, the protective film 28 is also located in the region between the reaction section 13 and at least one of the first IDT electrode 11 and the second IDT electrode 12, and does not cover the entire area of the reaction section 13. Furthermore, as shown in FIG. 6(b), an end of the protective film 28 located on a side of the reaction section 13 (the immobilization film 13a) comprises a lower end part and an upper end part, the end being inclined so as to approach the reaction section 13 (the immobilization film 13a) as the end going from the upper end part to the lower end part when viewed in a lateral section. This makes it possible to inhibit an analyte liquid from contact with the first IDT electrode 11 and the second IDT electrode 12 more effectively. Moreover, by forming the protective film 28 so as to cover the upper surface of the element substrate 10a, it is possible to enhance stability of connection with the element substrate 10a.

In this embodiment, a thickness of the protective film 28 may be set to fall within the range of $0.001\lambda$ to $0.05\lambda$, for example. While the measurement of the thickness of the protective film 28 may be made on a part thereof which covers neither the first IDT electrode 11 nor the second IDT electrode 12, the thickness measurement on other part will not be excluded herein.

A thickness of the protective film 28 may be set to be smaller than the thickness of the first IDT electrode 11 and the thickness of the second IDT electrode 12. This makes it possible to reduce the influence of the protective film 28 upon SAW propagating between the first IDT electrode 11 and the second IDT electrode 12, and thereby reduce losses of SAW energy. In this case, the upper surface of the protective film 28 may be, at least partly, positioned at a lower level than the upper surface of the first IDT electrode 11 and the upper surface of the second IDT electrode 12.

As shown in FIGS. 4 and 6, the first IDT electrode 11 and the second IDT electrode 12 include a plurality of electrode fingers which are spaced apart from each other, respectively, and, as shown in FIG. 6(b), the protective film 28 is made in continuous (connected) form so as to lie over, out of the plurality of electrode fingers, two adjacent electrode fingers, for example, the electrode fingers 12a and 12b, and also over that part of the element substrate 10a located between the two electrode fingers. This makes it possible to inhibit occurrence of short-circuiting between the plurality of electrode fingers of the IDT electrode caused by an analyte liquid.

(Extraction Electrodes 19 and 20)

As shown in FIG. 4, the first extraction electrode 19 is connected to the first IDT electrode 11, and the second extraction electrode 20 is connected to the second IDT electrode 12. The first extraction electrode 19 is extracted from the first IDT electrode 11 in the opposite direction to the reaction section 13, and, an end 19e of the first extraction electrode 19 is electrically connected to the wiring line 7 disposed in the first cover member 1. The second extraction electrode 20 is extracted drawn from the second IDT electrode 12 in the opposite direction to the reaction section 13, and, an end 20e of the second extraction electrode 20 is electrically connected to the wiring line 7.

The first extraction electrode 19 and the second extraction electrode 20 may be made similar in material and configuration to the first IDT electrode 11 and the second IDT electrode 12, and may thus be of a single-layer structure composed of, for example, a gold thin layer, or may be of a multilayer structure such as a three-layer structure composed of a titanium layer, a gold layer, and a titanium layer, or a three-layer structure composed of a chromium layer, a gold layer, and a chromium layer, in the order named, from the element-substrate 10a side.

(Detection of Object to be Detected Using Detecting Element 3)

To detect an object to be detected contained in an analyte liquid by the detecting element 3 which utilizes SAW as above described, a predetermined voltage from external measuring equipment is first applied to the first IDT electrode 11 via the wiring line 7, the first extraction electrode 19, and so forth.

Upon the voltage application, on the surface of the element substrate 10a, the first IDT electrode 11-forming region is excited, thus producing SAW having a predetermined frequency. Part of the SAW so generated propagates toward the reaction section 13, passes through the reaction section 13, and reaches the second IDT electrode 12. In the reaction section 13, the aptamer on the reaction section 13 is bound to a specific object to be detected contained in the analyte liquid, and the weight (mass) of the reaction section 13 changes correspondingly, which results in variation in the characteristics, such as a phase, of the SAW passing through the reaction section 13. In response to the arrival of the SAW having varied characteristics at the second IDT electrode 12, a corresponding voltage is developed in the second IDT electrode 12.

The thereby developed voltage is outputted through the second extraction electrode 20, the wiring line 70, and so forth. By reading the output with external measuring equipment, it is possible to examine the properties and constituents of the analyte liquid.

In the sensor apparatus 100, capillarity is utilized to direct the analyte liquid to the reaction section 13.

Specifically, as described earlier, when the second cover member 2 is joined to the intermediate cover member 1A, as shown in FIG. 1, the flow channel 15 is defined, in the form of a narrow elongate pipe, on the lower surface of the second cover member 2. Thus, by setting, for example, the width or the diameter of the flow channel 15 at a predetermined value with consideration given to the type of the analyte liquid, the materials of construction of the intermediate cover member 1A and the second cover member 2, and so forth, it is possible to cause capillarity in the flow channel 15 in the form of a narrow elongate pipe. For example, the flow channel 15 has a width of 0.5 mm to 3 mm, and a depth of 0.1 mm to 0.5 mm. As shown in FIG. 1(b), the flow channel 15 has a downstream portion (extension) 15b which is a portion extending beyond the reaction section 13, and, the second cover member 2 is formed with the air release hole 18 which is in communication with the extension 15b. Upon admission of the analyte liquid into the flow channel 15, air present in the flow channel 15 is expelled out of the air release hole 18.

With such a pipe form capable of causing capillarity defined by the cover members including the intermediate cover member 1A and the second cover member 2, upon contact with the inlet port 14, the analyte liquid is drawn into the interior of the sensor apparatus 100 while passing through the flow channel 15. Thus, the sensor apparatus 100 has an analyte liquid suction mechanism built in itself, and is therefore capable of analyte liquid suction without using an instrument such as a pipette.

(Positional Relationship Between Flow Channel 15 and Detecting Element 3)

In this embodiment, while the analyte-liquid flow channel 15 has a depth of about 0.3 mm, the detecting element 3 has a thickness of about 0.3 mm, that is; as shown in FIG. 1(b), the depth of the flow channel 15 and the thickness of the detecting element 3 are substantially equal. Therefore, if the detecting element 3 is placed as it is on the upper surface of the first cover member 1, the flow channel 15 will be blocked. In this regard, in the sensor apparatus 100, as shown in FIGS. 1(b) and 5, the element placement section 5 is defined by the first cover member 1 on which the detecting element 3 is mounted, and the intermediate cover member 1A joined onto the first cover member 1. The detecting element 3 is housed in this element placement section 5 so that the analyte-liquid flow channel 15 will not be blocked. That is, the depth of the element placement section 5 is adjusted to be substantially equal to the thickness of the detecting element 3, and, the detecting element 3 is mounted inside the element placement section 5. Thereby, the flow channel 15 can be provided.

The detecting element 3 is secured to the bottom surface of the element placement section 5 by, for example, a die-bonding material composed predominantly of resin such as epoxy resin, polyimide resin, or silicone resin.

The end 19e of the first extraction electrode 19 and the wiring line 7 are electrically connected to each other by a metallic narrow wire 27 formed of, for example, Au. The connection between the end 20e of the second extraction electrode 20 and the wiring line 7 is made in a similar way. Means for connecting the wiring line 7 with the first and second extraction electrodes 19 and 20 is not limited to the metallic narrow wire 27, but may be of an electrically-conductive adhesive such as a Ag paste. Since a gap is left in the part where the wiring line 7 makes connection with each of the first and second extraction electrodes 19 and 20, it is possible to suppress damage of the metallic narrow wire 27 when bonding the second cover member 2 to the first cover member 1. Moreover, the first extraction electrode 19, the second extraction electrode 20, the metallic narrow wire 27, and the wiring line 7 are covered with the protective film 28. By covering the first extraction electrode 19, the second extraction electrode 20, the metallic narrow wire 27, and the wiring line 7 with the protective film 28, it is possible to suppress corrosion of these electrodes and the like.

As described heretofore, according to the sensor apparatus 100 in the embodiment, by placing the detecting element 3 in the element placement section 5 of the first cover member 1, it is possible to provide the analyte-liquid flow channel 15 extending from the inlet port 14 to the reaction section 13, and thereby allow the analyte liquid, which has been drawn into the apparatus through the inlet port 14 under capillarity for example, to flow to the reaction section 13. That is, even with use of the detecting element 3 having a certain thickness, since the sensor apparatus 100 has an analyte liquid suction mechanism built in itself, it is possible to provide a sensor apparatus 100 capable of directing an analyte liquid to the detecting element 3 efficiently.

<Manufacturing Process of Detecting Element>

Figure 7:
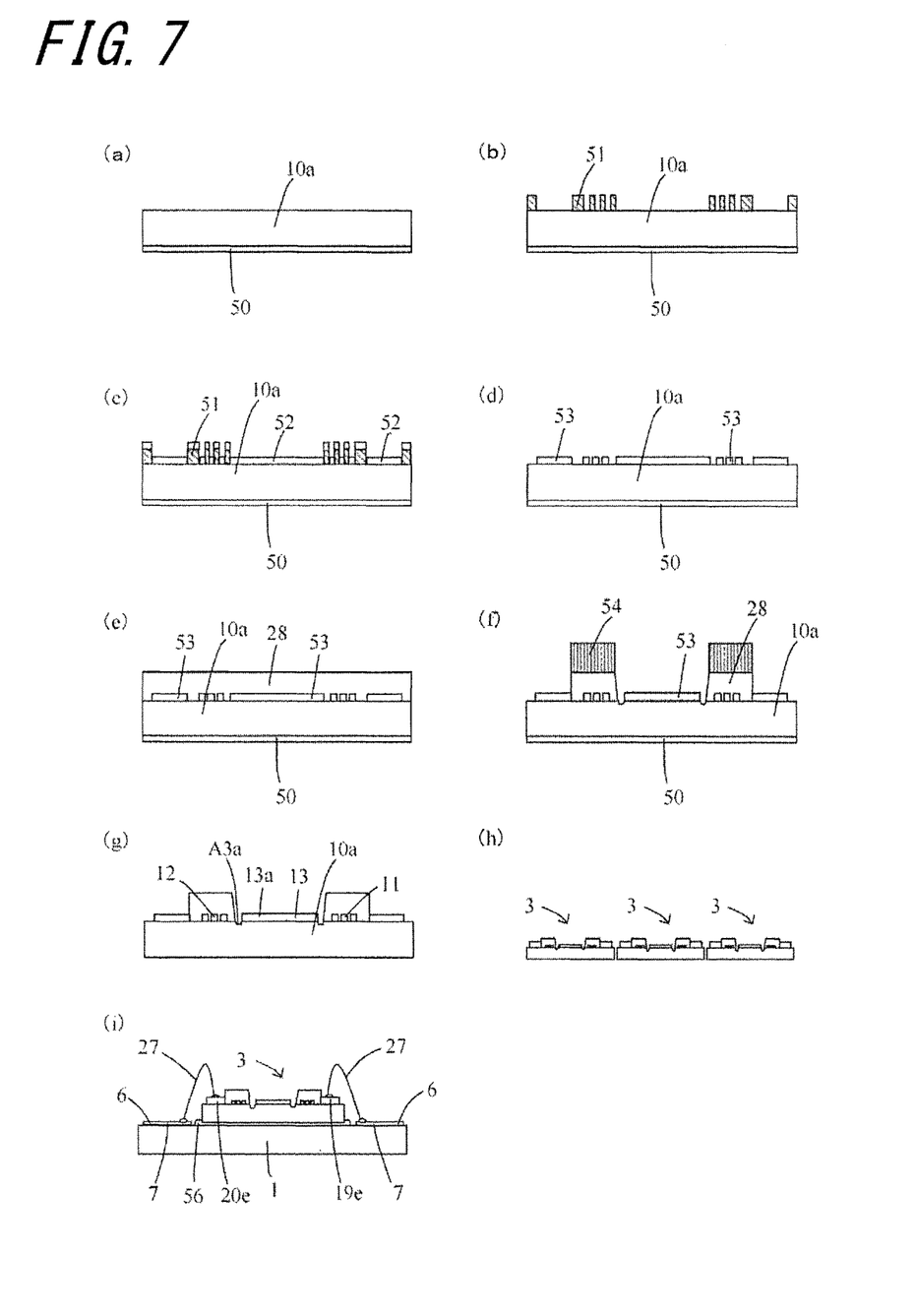
FIG. 7 is a schematic view showing procedural steps to manufacture the detecting element 3.

The following describes a procedure in the making of the detecting element 3 provided in the sensor apparatus 100 according to the embodiment of the invention. FIG. 7 is a schematic view showing procedural steps for manufacturing the detecting element 3.

First, a quartz-made element substrate 10a is washed. After that, on an as needed basis, an Al film is formed on the lower surface of the element substrate 10a by RF sputtering technique (FIG. 7(a)).

Next, an electrode pattern is formed on the upper surface of the element substrate 10a. In this step, a photoresist pattern 51 of image reversal type for electrode-pattern formation is formed by photolithography technique (FIG. 7(b)).

Next, a metallic layer 52 having a three-layer structure composed of Ti/Au/Ti layers is formed on each of a photoresist pattern 51-bearing part and a photoresist pattern 51-free part of the upper surface of the element substrate 10a by electron-beam vapor deposition equipment (FIG. 7(c)).

Next, a Ti/Au/Ti electrode pattern 53 is formed by lifting off the photoresist pattern 51 using a solvent, followed by oxygen-plasma ashing treatment (FIG. 7(d)).

In this embodiment, the Ti/Au/Ti electrode pattern 53 defines, in addition to a pair of IDT electrodes 11 and 12 and the immobilization film 13a, a reflector (not shown in the drawing) and mounting extraction electrodes 19 and 20. The pair of IDT electrodes 11 and 12 is disposed so as to face each other, and, one of them serves as a transmitter, whereas the other serves as a receiver. Thus, the pair of IDT electrodes 11 and 12, the immobilization film 13a, the reflector, and the mounting extraction electrodes 19 and 20 can be formed in one process step.

Next, a protective film 28 is formed on the upper surface of the element substrate 10a so as to cover the Ti/Au/Ti electrode pattern 53 by, for example, TEOS (Tetra Ethyl Ortho Silicate)-plasma CVD technique (FIG. 7(e)).

Next, a protective film 28 pattern is formed by forming a positive photoresist 54 on the upper surface of the protective film 28, followed by etching of the protective film 28 using RIE equipment (FIG. 7(f)).

Specifically, the positive photoresist 54 is formed on the upper surface of the protective film 28 which covers each of the IDT electrodes 11 and 12, and, following the completion of etching of the positive photoresist 54-free part of the protective film 28 using the RIE equipment, the positive photoresist 54 is lifted off with use of a solvent, whereupon the protective film 28 pattern for covering the IDT electrodes 11 and 12 is formed. At this time, in the third region A3 which is located between the first region A1 where the first IDT electrode 11 and the second IDT electrode 12 are located and the second region A2 where the reaction section 13 is located, the recess A3a is formed so as to be at a lower level than the first region A1 and the second region A2 by performing overetching on the element substrate 10a. Moreover, by etching using the RIE equipment, the protective film 28 is removed from a photoresist 54-free part of the Ti/Au/Ti electrode pattern 53, and also the outermost Ti layer of the Ti/Au/Ti electrode pattern 53 is etched. In this way, as contrasted to the above-described embodiment, a part of the immobilization film 13a which is not covered with the protective film 28 may be given a two-layer structure composed of Au/Ti layers. This makes it possible to obtain an arrangement in which the immobilization film 13a having a two-layer structure composed of Au/Ti layers is located between the paired IDT electrodes 11 and 12 having a three-layer structure composed of Ti/Au/Ti layers. Given that the paired IDT electrodes 11 and 12 of Ti/Au/Ti three-layer structure and the immobilization film 13a of Au/Ti two-layer structure are grouped into a set, then there are provided two sets on a single element substrate 10a. One of the two sets is used as a set for "detection", whereas the other is used as a set for "reference". Note that, as is the case with the immobilization film 13a, also in the process of forming the reflector and the mounting extraction electrodes 19 and 20, the outermost Ti layer may be subjected to etching.

After that, the Al film 50 formed on the lower surface of the element substrate 10a is removed with use of fluonitric acid.

A nucleic acid- or peptide-made aptamer is immobilized on the upper surface of the immobilization film 13a to form the reaction section 13 (FIG. 7(g)).

In the manner as described heretofore, the detecting element 3 is formed.

Next, the element substrate 10a is cut in a predetermined size by dicing (FIG. 7(h)). After that, separate detecting elements 3 obtained by cutting process are fixedly attached, at their back sides, onto a wiring-equipped glass epoxy mounting substrate (hereafter referred to as "mounting substrate") corresponding to the first cover member 1 with use of an epoxy adhesive 56. Then, using Au narrow wires as the lead wires 27, electrodes 19e and 20e of the extraction electrodes disposed on the detecting element 3 and the wiring lines 7 connected to terminals 6 disposed on the mounting substrate are electrically connected (FIG. 7(i)).

Following the completion of placement of the intermediate cover member 1A, the second cover member 2, and so forth, the sensor apparatus 100 in accordance with the embodiment of the invention is formed.

The manufacturing process of the detecting element 3, as well as the manufacturing process of the sensor apparatus 100, is not limited to the aforestated procedure shown in FIG. 7, and it is thus possible to adopt any other manufacturing process that enables production of the element substrate 10a whose upper surface is configured so that the region 10a2 where the reaction section 13 is located is lower than the regions 10a1 where the first IDT electrode 11 and the second IDT electrode 12 are located.

The invention is not limited to the embodiment thus far described, and may therefore be carried into effect in various forms.

Although the embodiment has been described with respect to the case where the reaction section 13 comprises the immobilization film 13a and the aptamer immobilized on the upper surface of the immobilization film 13a, the constituent element is not limited to the aptamer. As an alternative to the aptamer which is immobilized on the upper surface of immobilization film 13a, it is possible to use a reactant which undergoes reaction with an object to be detected contained in an analyte liquid and causes variation in SAW characteristics before and after analyte passage through the reaction section 13. Moreover, for example, in cases where the object to be detected in the analyte liquid reacts with the immobilization film 13a, the reaction section 13 may be composed solely of the immobilization film 13a without using the aptamer. Furthermore, the reaction section 13 may be defined by a region between the first IDT electrode 11 and the second IDT electrode 12 on the surface of the element substrate 10a constructed of a piezoelectric substrate without using the immobilization film 13a. In this case, an analyte liquid is applied directly to the surface of the element substrate 10a to detect the physical properties, including the viscosity, of the analyte liquid. More specifically, SAW phase variation resulting from a change in, for example, the viscosity of the analyte liquid on the reaction section 13 is monitored. Moreover, instead of a metallic film, a non-conductive film may be used as the immobilization film 13a, and, in this case, the aptamer is immobilized on the upper surface of the non-conductive film.

Moreover, the detecting element 3 may be constructed of a single substrate on which a variety of devices are disposed. For example, an enzyme electrode for use with enzyme electrode method may be disposed next to a SAW device. In this case, in addition to measurement based on the immuno method using an antibody or aptamer, measurement based on the enzymatic method can also be conducted, thus increasing the number of measurement points that can be checked at one time.

Moreover, while the embodiment has been described with respect to the case of providing a single detecting element 3, a plurality of detecting elements 3 may be provided. In this case, the element placement section 5 is formed for each detecting element 3 on an individual basis, or, the element placement section 5 is configured to have a length or width large enough to receive all of the detecting elements 3.

Moreover, while the embodiment has been described with respect to the case where the first cover member 1, the intermediate cover member 1A, and the second cover member 2 are provided as separate components, this does not constitute any limitation, and thus either a combination of some of these members in an unitary structure or a combination of all the members in an unitary structure may be adopted.

REFERENCE SIGNS LIST

1: First cover member
1A: Intermediate cover member
   1Aa: First upstream portion
2: Second cover member
   2a: Third substrate
   2b: Fourth substrate
3: Detecting element
4: Recess-forming area
5: Element placement section
6: Terminal
7: Wiring line
9: Filler member
10a: Element substrate
   A1: First region
   A2: Second region
   A3: Third region
      A3a: Recess
   10b: Detecting section
11: First IDT electrode
12: Second IDT electrode
13: Reaction section
   13a: Immobilization film
14: Inlet port
15: Flow channel
   15a: Upstream portion
   15b: Downstream portion (extension)
18: Air release hole
19: First extraction electrode
   19e: End
20: Second extraction electrode
   20e: End
27: Lead wire (metallic narrow wire)
28: Protective film
100: Sensor apparatus

The invention claimed is:

1. A sensor apparatus, comprising:
an element substrate;
a detecting section disposed on an upper surface of the element substrate, the detecting section comprising a reaction section having an immobilization film to detect an analyte, a first IDT electrode configured to generate an acoustic wave which propagates toward the reaction section, and a second IDT electrode configured to receive the acoustic wave which has passed through the reaction section; and a protective film which covers the first IDT electrode and the second IDT electrode, wherein the upper surface of the element substrate comprises a first region where the first IDT electrode and the second IDT electrode are located, a second region where the reaction section is located, and a third region which is located between the first region and the second region, at least part of the third region being lower in level than the first region and the second region.

2. The sensor apparatus according to claim 1,
wherein the element substrate comprises a recess located in the at least part of the third region, the recess being tapered so as to narrow gradually with approaching toward a bottom thereof as viewed in a lateral section of the recess.

3. The sensor apparatus according to claim 2,
wherein part of the protective film is located in a part of the third region, the part of the third region being located between the recess and at least one of the first IDT electrode and the second IDT electrode.

4. The sensor apparatus according to claim 1,
wherein part of the protective film is located in the third region.

5. The sensor apparatus according to claim 1,
wherein part of the protective film is located between the immobilization film and at least one of the first IDT electrode and the second IDT electrode.

6. The sensor apparatus according to claim 1,
wherein the protective film is spaced away from the immobilization film.

7. The sensor apparatus according to claim 1,
wherein an upper surface of the immobilization film is at a lower level than at least one of an upper surface of the first IDT electrode and an upper surface, of the second IDT electrode.

8. The sensor apparatus according to claim 1,
wherein a material of the immobilization film is a same as a material of the first IDT electrode and a material of the second IDT electrode.

9. The sensor apparatus according to claim 1,
wherein a thickness of the immobilization film is smaller than at least one of a thickness of the first IDT electrode and a thickness of the second IDT electrode.

10. The sensor apparatus according to claim 1,
wherein a surface roughness of an upper surface of the immobilization film is greater than at least one of a surface roughness of an upper surface of the first IDT electrode and a surface roughness of an upper surface of the second IDT electrode.

11. The sensor apparatus according to claim 1,
wherein an end of the protective film located on a side of the immobilization film comprises a lower end part and an upper end part, the lower end part being closer to the immobilization film than the upper end part when viewed in a lateral section.

12. The sensor apparatus according to claim 1,
wherein an end of the protective film located on a side of the immobilization film comprises a lower end part and an upper end part, the end being inclined so as to approach the immobilization film as the end going from the upper end part to the lower end part when viewed in a lateral section.

13. The sensor apparatus according to claim 1,
wherein an end of the immobilization film located on at least one of a side of the first IDT electrode and a side of the second IDT electrode comprises a lower end part and an upper end part, the lower end part being closer to the at least one of a side of the first IDT electrode and a side of the second IDT electrode than the upper end part when viewed in a lateral section.

14. The sensor apparatus according to claim 1,
wherein an end of the immobilization film located on at least one of a side of the first IDT electrode and a side of the second IDT electrode comprises a lower end part and an upper end part, the end being inclined so as to approach the at least one of a side of the first IDT electrode and a side of the second IDT electrode as the end going from the upper end part to the lower end part when viewed in a lateral section.

15. The sensor apparatus according to claim 14,
wherein an end of the protective film located on a side of the immobilization film comprises a lower end part and an upper end part, the end being inclined so as to approach the immobilization film as the end going from the upper end part to the lower end part when viewed in a lateral section, and an angle of inclination of the end of the immobilization film is smaller than an angle of inclination of the end of the protective film.

* * * * *